US012611340B2

(12) United States Patent
Corneliusson et al.

(10) Patent No.: US 12,611,340 B2
(45) Date of Patent: *Apr. 28, 2026

(54) ABSORBENT INSERT

(71) Applicant: Essity Hygiene and Health Aktiebolag, Gothenburg (SE)

(72) Inventors: Helena Corneliusson, Gothenburg (SE); Mattias Johansson, Gothenburg (SE); Ulla Danielsson, Gothenburg (SE); Peter Axborn, Gothenburg (SE); Karoline Lenhult, Lidköping (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 238 days.

This patent is subject to a terminal disclaimer.

(21) Appl. No.: 18/551,418

(22) PCT Filed: Apr. 7, 2021

(86) PCT No.: PCT/SE2021/050313
§ 371 (c)(1),
(2) Date: Sep. 20, 2023

(87) PCT Pub. No.: WO2022/216188
PCT Pub. Date: Oct. 13, 2022

(65) Prior Publication Data
US 2024/0164959 A1 May 23, 2024

(51) Int. Cl.
*A61F 13/494* (2006.01)
*A61F 13/49* (2006.01)
*A61F 13/505* (2006.01)
(52) U.S. Cl.
CPC ...... *A61F 13/505* (2013.01); *A61F 13/49009* (2013.01); *A61F 13/49017* (2013.01); *A61F 13/49413* (2013.01); *A61F 2013/4944* (2013.01)

(58) Field of Classification Search
CPC ............ A61F 13/15268; A61F 13/4752; A61F 13/4753; A61F 13/49413; A61F 13/4942;
(Continued)

(56) References Cited

U.S. PATENT DOCUMENTS 4,597,760 A * 7/1986 Buell ..................... A41B 13/04
604/397
4,795,454 A 1/1989 Dragoo et al.
(Continued)

FOREIGN PATENT DOCUMENTS

CN 105828767 A 8/2016
CN 108601693 A 9/2018
(Continued)

OTHER PUBLICATIONS

International Search Report (PCT/ISA/210) and Written Opinion (PCT/ISA/237) mailed on Nov. 22, 2021, by the Swedish Patent Office as the International Searching Authority for International Application No. PCT/SE2021/050313.
(Continued)

*Primary Examiner* — Catharine L Anderson
(74) *Attorney, Agent, or Firm* — BUCHANAN INGERSOLL & ROONEY PC

(57) ABSTRACT

The disposable absorbent insert for a reusable outer shell has an extension in the longitudinal direction and the transversal direction, longitudinal and transversal side edges and having a front portion, a back portion and a crotch portion located between the front and the back portions. The insert includes an absorbent core having longitudinal and transversal side edges and being sandwiched between a liquid-permeable and user facing topsheet and a liquid-impermeable and garment facing backsheet and wherein the absorbent core includes an absorbent component enclosed by a core cover including an upper and a lower side. The insert further
(Continued)

includes a first longitudinal extending standing gather along a first longitudinal side edge of the insert and a second longitudinal extending standing gather along a second longitudinal side edge of the insert.

29 Claims, 4 Drawing Sheets

(58) Field of Classification Search
CPC .. A61F 13/49453; A61F 13/505; A61F 13/66; A61F 13/70; A61F 2013/15276; A61F 2013/49092; A61F 2013/49093; A61F 2013/4944; A61F 2013/4948; A61F 2013/49493; A61F 2013/5055
See application file for complete search history.

(56) References Cited

U.S. PATENT DOCUMENTS

| | | | |
|---|---|---|---|
| 4,846,825 A | 7/1989 | Enloe et al. | |
| 6,468,257 B1 * | 10/2002 | Ono | A61F 13/505 604/385.01 |
| 6,575,951 B1 * | 6/2003 | Ono | A61F 13/505 604/391 |
| 7,875,014 B2 * | 1/2011 | Hendren | A61F 13/565 604/396 |
| 7,993,322 B2 * | 8/2011 | Brud | A61F 13/66 604/397 |
| 8,932,273 B2 * | 1/2015 | Roe | A61F 13/5638 604/385.28 |
| 10,786,403 B2 | 9/2020 | Bianchi et al. | |
| 2006/0116656 A1 | 6/2006 | Hendren et al. | |
| 2010/0179496 A1 | 7/2010 | Roe et al. | |
| 2011/0137278 A1 | 6/2011 | Ormsby et al. | |
| 2013/0006209 A1 | 1/2013 | Ruiz | |
| 2014/0005621 A1 | 1/2014 | Roe et al. | |
| 2014/0257231 A1 | 9/2014 | Wang et al. | |
| 2015/0223995 A1 | 8/2015 | Martynus et al. | |
| 2018/0311081 A1 | 11/2018 | Hood et al. | |
| 2019/0117471 A1 | 4/2019 | Brownlee | |
| 2019/0133845 A1 | 5/2019 | Johansson et al. | |
| 2021/0251818 A1 | 8/2021 | Roe et al. | |
| 2024/0164958 A1 | 5/2024 | Corneliusson et al. | |
| 2025/0131382 A1 | 4/2025 | Williams | |

FOREIGN PATENT DOCUMENTS

| | | | |
|---|---|---|---|
| CN | 109310551 A | 2/2019 | |
| EP | 1097687 A2 | 5/2001 | |
| EP | 1101469 A2 | 5/2001 | |
| EP | 3981371 A1 | 4/2022 | |
| JP | 2008538984 A | 11/2008 | |
| JP | 2010269002 A | 12/2010 | |
| JP | 2012515058 A | 7/2012 | |
| JP | 2014198074 A | 10/2014 | |
| JP | 2016502871 A | 2/2016 | |
| JP | 2019146939 A | 9/2019 | |
| WO | 2010134589 A1 | 11/2010 | |
| WO | 2014138276 A1 | 9/2014 | |
| WO | 2020210999 A1 | 10/2020 | |
| WO | 2020241557 A1 | 12/2020 | |
| WO | 2021163258 A1 | 8/2021 | |

OTHER PUBLICATIONS

The extended European Search Report issued on Nov. 18, 2024, by the European Patent Office in corresponding European Application No. 21936176.3. (7 pages).

International Preliminary Report on Patentability (Forms PCT/IB/ 326 and PCT/IB/373) issued on Oct. 19, 2023, by the International Bureau of WIPO, in corresponding International Application No. PCT/SE2021/050313. (2 pages).

Office Action (Notice of Reasons for Rejection) issued on Sep. 2, 2024, by the Japanese Patent Office in corresponding Japanese Patent Application No. 2023-561817, and an English Translation of the Office Action. (9 pages).

International Preliminary Report on Patentability of the International Bureau of WIPO (Forms PCT/IB/326 and PCT/IB/373) issued on Oct. 19, 2023, by the International Bureau of WIPO, in corresponding International Application No. PCT/SE2021/050439. (2 pages).

International Search Report and Written Opinion of the International Searching Authority (Forms PCT/ISA/220, PCT/ISA/210 and PCT/ISA/237) issued on Nov. 22, 2021, by the International Bureau of European Patent Office in corresponding International Application No. PCT/SE2021/050439. (17 pages).

Office Action (Notice of Reasons for Rejection) issued on Aug. 26, 2024, by the Japanese Patent Office in corresponding Japanese Patent Application No. 2023-561816, and an English Translation of the Office Action. (10 pages).

The Examiner's attention is directed to co-pending U.S. Appl. No. 18/551,041, filed Sep. 18, 2023.

The extended European Search Report issued on Jan. 9, 2025, by the European Patent Office in corresponding European Application No. 21936179.7. (8 pages).

Office Action (Notification of the First Office Action) issued on Dec. 27, 2025, by the Chinese Patent Office in corresponding Chinese Patent Application No. 202180096754.X, and an English Translation of the Office Action. (17 pages).

Notice of Allowance issued on Mar. 13, 2026, by the U.S. Patent and Trademark Office in U.S. Appl. No. 18/551,041 (16 pages).

* cited by examiner

FIG. 2   A-A

ABSORBENT INSERT

TECHNICAL FIELD

The disclosure relates to an absorbent insert for a reusable outer shell and a wearable absorbent article comprising a reusable shell and a disposable insert.

BACKGROUND

Wearable and disposable absorbent articles, for example in the form of diapers, incontinence garments, feminine garments, inserts and the like, are well known. Absorbent articles are used to absorb, distribute and store various types of body exudates while providing a high level of comfort and sense of dryness to the wearer during use.

A conventional disposable absorbent article in the form of a diaper is normally designed with an absorbent core which is sandwiched between a topsheet and a backsheet. The article is arranged along a longitudinal axis and along a transversal axis which extends in a perpendicular direction in relation to the longitudinal axis. Furthermore, the article can be divided into a front portion, a back portion and a crotch portion. The diaper is designed with a waist portion to be enclosing the wearer being integral with the core and further comprising interior leg gathers i.e. standing gathers, and exterior leg gathers to avoid edge leakages from the article.

A disposable absorbent insert is to be used with an outer reusable shell and is normally of a simpler design than a disposable diaper as it is intended to be used with an exterior disposable or reusable shell or cover.

US20190117471A1 discloses an absorbent channel insert diaper adapted for removable use in a supporting shell, or as a multiplier in a single-use disposable diaper.

SUMMARY

The present disclosure is based on the insight that disposable inserts without exterior leg cuffs may in certain instances suffer from edge leakages or soiling.

The present invention provides an absorbent insert in accordance with claim 1 and a wearable absorbent article comprising a reusable shell and a disposable insert according to claim 29 alleviating the above problem. Further embodiments are set out in the dependent claims and in the following description.

The disposable absorbent insert for a reusable outer shell has an extension in the longitudinal direction and the transversal direction, longitudinal and transversal side edges and having a front portion, a back portion and a crotch portion located between the front and the back portions. The insert comprises an absorbent core having longitudinal and transversal side edges and being sandwiched between a liquid-permeable and user facing topsheet and a liquid-impermeable and garment facing backsheet and wherein the absorbent core comprises an absorbent component enclosed by a core cover comprising an upper and a lower side. The insert further comprises a first longitudinal extending standing gather along a first longitudinal side edge of the insert and a second longitudinal extending standing gather along a second longitudinal side edge of the insert. The insert has a first side leakage flap extending transversely outside the first longitudinal extending standing gather and a second leakage flap extending transversely outside the second longitudinal extending standing gather.

The side leakage flaps of the insert are capable of preventing body liquids, that may have escaped absorption in the absorbent core of the insert, from soiling the leg surrounding parts of a reusable shell to be used in combination with the disposable insert. This is an advantage for an absorbent insert that lacks elastics at a free outer longitudinal side edge of the insert or in other words lacks exterior leg gathers.

The first side leakage flap may extend along the whole longitudinal length of the first longitudinal side edge of the insert and the second leakage flap may extend along the whole longitudinal length of the second longitudinal side edge of the insert.

The first and second side leakage flaps may be extensions of the topsheet and the backsheet. The first and second side leakage flaps may be extensions of the topsheet, backsheet and first and second respectively standing gather materials. The topsheet and the backsheet in the first and second side leakage flaps may be attached to each other, such as by adhesive. The topsheet and the standing gather materials in the first and second side leakage flaps may be attached to each other, such as by a longitudinal welding line and/or a line of adhesive. The standing gather materials and the backsheet in the first and second side leakage flaps respectively may be attached to each other. The lamination strength between the materials in the side leakage flaps may be more than 2 N/25 mm.

The first longitudinal standing gather extending along a first longitudinal side edge of the insert may comprise a first sheet of material and an elastic thread and a second longitudinal standing gather extending along a second longitudinal side edge of the insert may comprise a second sheet of material and an elastic thread. The first and second standing gather respectively may comprise more than one elastic thread, such as 2-5 elastic threads. The material of the first and second standing gather respectively may comprise two layers of material. The material of the first and second standing gather may be attached to the topsheet material in the first and second side leakage flaps respectively. The attachment may be a longitudinal welding line and/or a line of adhesive. The material of the first standing gather may comprise a part being attached to the topsheet and a part being non-attached to the topsheet comprising the elastic thread. The material of the second standing gather may comprise a part being attached to the topsheet and a part being non-attached to the topsheet comprising the elastic thread. The elastic thread of the first and second standing gather respectively may be raised above the user facing surface of the topsheet. The elastic thread of the first and second standing gather respectively may be raised at least 20 mm and less than 70 mm, such as at least 30 mm and less than 50 mm above the user facing surface of the topsheet.

The transverse extension of the first and second side leakage flaps respectively may be at least 10 mm and less than 70 mm, such as at least 15 mm and less than 60 mm, such as at least 25 mm and less than 50 mm, such as 10-40 mm, as measured from a point of intersection between a part of the material of the standing gather being attached to the topsheet and a part of the material of the standing gather being non-attached to the topsheet comprising an elastic thread and to the closest longitudinal side edge of the insert.

The topsheet and the backsheet may extend longitudinally outside the transversal side edges of the core in the front and back portions respectively of the insert. The longitudinal extension of the topsheet and backsheet may be greater in the back portion of the insert than in the front portion of the insert. The extension of the topsheet and backsheet in the back portion may be 2 to 6 times greater than in the front portion of the insert, optionally 3-5 times greater.

A strip of loop material may be attached to the garment facing surface of the backsheet near the transversal side edge of the front and back portions respectively of the insert. The strip of loop material may extend over 50-100%, such as 70-90% of the transverse side of the insert. The longitudinal extension of the strip of loop material may be 10 to 50 mm, optionally 10 to 35 mm. The longitudinal extension of the strip of loop material may be greater in the back portion than in the front portion of the insert. The strip of loop material may have the same free transversal side edge as materials of the topsheet and the backsheet. The strip of loop material may have the same free transversal side edge as the insert.

The core may have a rectangular shape. The insert may have a rectangular shape.

There is further provided a wearable absorbent article comprising a reusable shell to be worn by a wearer, and a disposable insert as described herein.

In addition, there is provided a disposable absorbent insert for a reusable outer shell, the insert having an extension in the longitudinal direction and the transversal direction, longitudinal and transversal side edges and having a front portion, a back portion and a crotch portion located between the front and the back portions, and comprising an absorbent core having longitudinal and transversal side edges and being sandwiched between a liquid-permeable and user facing topsheet and a liquid-impermeable and garment facing backsheet and wherein the absorbent core comprises an absorbent component enclosed by a core cover comprising an upper and a lower side, the insert comprising a first longitudinal extending standing gather along a first longitudinal side edge of the insert and a second longitudinal extending standing gather along a second longitudinal side edge of the insert, wherein a strip of loop material is attached to a garment facing side of the backsheet near the transverse side edge of the front portion and back portion respectively of the insert.

The strip of loop material may extend over 50-100% of the transversal side of the insert. The longitudinal extension of the strip of loop material may be 10 to 50 mm, such as 10 to 35 mm. The longitudinal extension of the strip of loop material may be greater in the back portion than in the front portion of the insert. The strip of loop material may have the same free transversal side edge as materials of the topsheet and the backsheet. The strip of loop material may have the same free transversal side edge as the insert. The insert with the strips of loop material attached to the backsheet may further comprise any other feature of the insert as disclosed above and herein.

A wearable absorbent article comprising a reusable shell, to be worn by a wearer, may comprise a disposable insert comprising a strip of loop material attached to the garment facing side of the backsheet near the transverse side edge of the front and back portions respectively of the insert, as disclosed above.

The strips of loop material on the garment facing side of the backsheet provide improved attachment of the insert into a reusable shell provided with hook patches at an inside of a front and back portion thereof such as disclosed herein. The production of the insert is facilitated in that a loop material normally used as a landing zone on a normal diaper may be cut and used as strips of loop material for the insert as disclosed above. The attachment of the loop material may continuously be made during production by adding a loop material to bridge the outline of two nearby inserts that are still connected by continuous topsheet and backsheet materials. The inserts are thereafter separated by cutting through the loop material and the topsheet and backsheet materials in one cutting operation to thereby separate the connected inserts. The strip of loop material in the front and back portions respectively of the insert will thereby have the same free transversal side edge as the materials of the topsheet and the backsheet, i.e. as the insert itself. An advantage of an insert having a strip of loop material in the front and back portion thereof with the same free transversal side edges as the insert itself is that it will provide improved and close attachment of the insert, when in use, in a reusable shell.

The insert and the wearable absorbent article comprising a reusable shell and a disposable insert as disclosed herein is for industrial production.

Further advantages and advantageous features of the disclosure are disclosed in the following description and in the dependent claims.

BRIEF DESCRIPTION OF THE DRAWINGS

The disclosure will be described in greater detail below with reference to the figures shown in the appended drawings, wherein FIG. 2 shows a cross-sectional view of the insert in FIG. 1.

DETAILED DESCRIPTION

Different aspects of the present disclosure will be described more fully hereinafter with reference to the enclosed drawings. The embodiments of the insert disclosed herein can, however be realized in many different forms, such as different sizes and absorption levels, and should not be construed as being limited to the aspects set forth herein.

Figure 1:
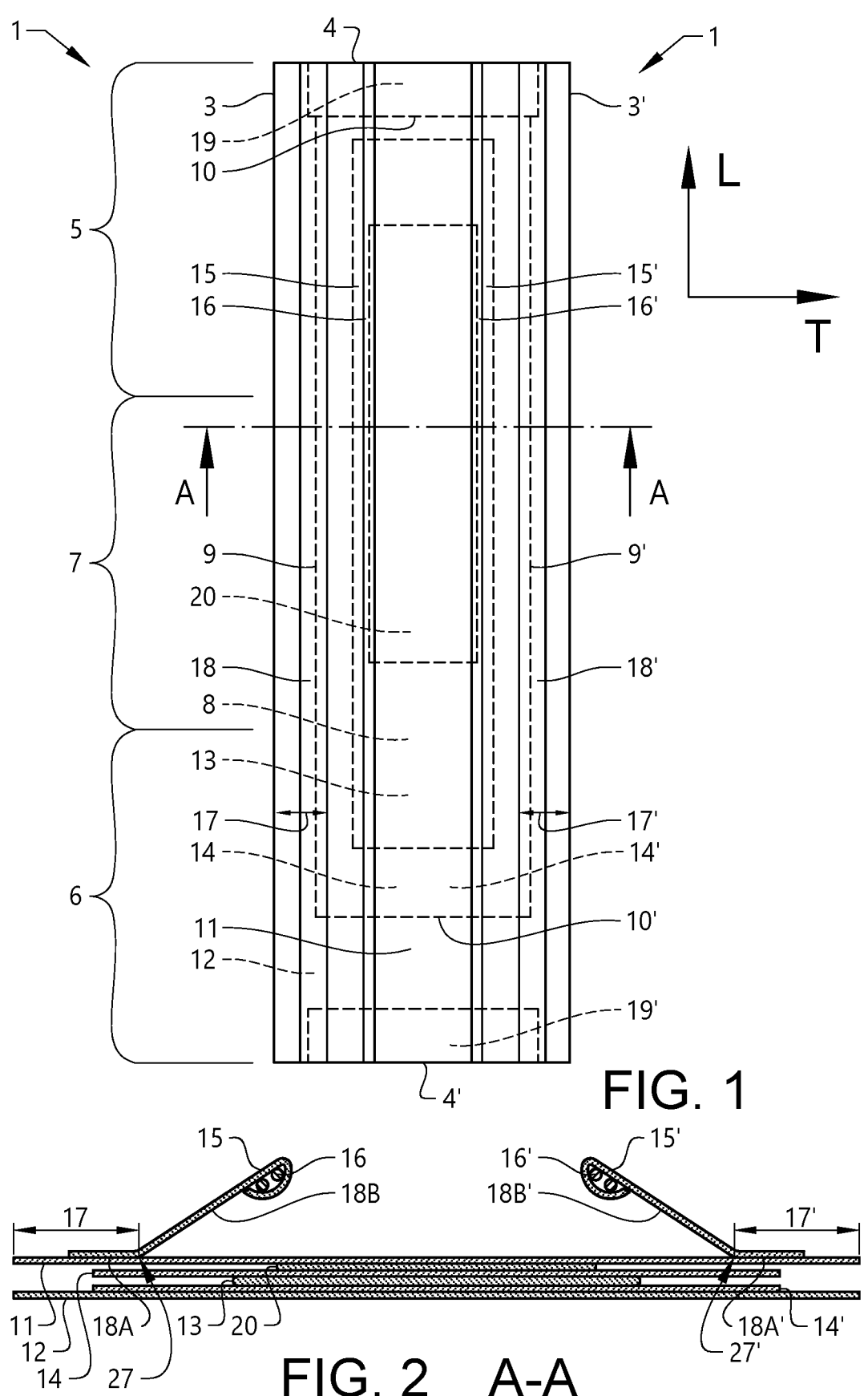
FIG. 1 shows a plan view from above of an absorbent insert according to the present disclosure.

FIG. 1 discloses a disposable absorbent insert 1 for a reusable outer shell 2 having an extension in the longitudinal direction L and the transversal direction T. The insert 1 has longitudinal 3, 3' and transversal 4, 4' side edges and having a front portion 5, a back portion 6 and a crotch portion 7 located between the front 5 and the back 6 portions. The insert 1 comprises an absorbent core 8 having longitudinal 9, 9' and transversal 10, 10' side edges and being sandwiched between a liquid-permeable and user facing topsheet 11 and a liquid-impermeable and garment facing backsheet 12. The absorbent core 8 comprises an absorbent component 13 enclosed by a core cover comprising an upper 14 and a lower 14' side. Sealing arrangements is arranged to seal the upper 14 and lower 14' core cover sides at their side edges (not shown). An acquisition layer 20 may be located between the topsheet 11 and the absorbent core 8. The insert 1 further comprises a first longitudinal extending standing gather 15 along a first longitudinal side edge 3 of the insert and a second longitudinal extending standing gather 15' along a second longitudinal side edge 3' of the insert 1. The insert 1 has a first side leakage flap 17 extending transversely outside the first longitudinal extending standing gather 15 and a second leakage flap 17' extending transversely outside the second longitudinal extending standing gather 15'. The first 17 and second 17' side leakage flap respectively extend along the whole longitudinal length of the first 3 and second 3' longitudinal side edge respectively of the insert but may have a shorter extension.

The first 17 and second 17' side leakage flaps are extensions of the topsheet 11 and the backsheet 12 but may also include an extension of the materials 18, 18' of the first 15 and second 15' respectively standing gather, or be an extension of the backsheet 12 and the materials 18, 18' of the first 15 and second 15' respectively standing gather. The topsheet 11 and the backsheet 12 in the first 17 and second 17' side leakage flaps is attached to each other, such as by adhesive. The topsheet 11 and the standing gather materials 18, 18' of the first 17 and second 17' side leakage flaps are attached to each other such as by a longitudinal welding line and/or a line of adhesive. The standing gather materials 18, 18' and the backsheet 12 in the first 17 and second 17' side leakage flaps may be attached to each other in case of a shorter lateral extension of the topsheet 11 than the materials of the standing gather 18, 18'. The lamination strength between the different materials in the side leakage flaps 17, 17' may be more than 2 N/25 mm.

The topsheet 11 and the backsheet 12 extend longitudinally outside the transversal side edges 10, 10' of the core 8 in the front 5 and back 6 portions respectively of the insert 1. The longitudinal extension of the topsheet 11 and backsheet 12 is greater in the back 6 portion of the insert 1 than in the front 5 portion of the insert 1. The extension of the topsheet 11 and backsheet 12 in the back 6 portion may be 2 to 6 times greater than in the front 5 portion of the insert 1.

A strip of loop material 19, 19' is attached to the garment facing side of the backsheet 12 near the transversal side 4, 4' edge of the front 5 and back 6 portions respectively of the insert 1. The strip of loop material 19, 19' extends over 50-100% of the transverse side of the insert 1. The longitudinal extension of the strip of loop material is 10 to 50 mm. The longitudinal extension of the strip of loop material 19, 19' may be greater in the back portion 6 than in the front portion 5 of the insert 1. The strip of loop material 19, 19' have the same free transversal side edge 4, 4' as materials of the topsheet 11 and the backsheet 12.

The core 8 has a rectangular shape. The insert 1 has a rectangular shape.

FIG. 2 shows a cross-sectional view A-A of the insert in FIG. 1. Starting from the lowermost layer being the backsheet 12, followed by the lower core cover layer 14', the absorbent component 13, the uppermost core cover layer 14, the acquisition layer 20 and the topsheet 11. The standing gathers 15, 15' are located at the respective longitudinal side edges 3, 3' of the insert 1. The respective standing gathers 15, 15' comprises a material 18, 18' and at least one elastic thread 16, 16', wherein two elastic threads 16, 16' are shown in FIG. 2 for each standing gather 15, 15'. The material 18, 18' of the standing gather 15, 15' comprises a material, such as a water impermeable nonwoven material, wherein a part of the material 18A, 18A' is attached to the topsheet 11, such as by a longitudinal welding line and/or a line of adhesive, and a part of the material 18B, 18B' is non-attached to the topsheet 11 and comprises the elastic thread. The transverse extension of the first 17 and second 17' side leakage flaps respectively may be at least 10 mm and less than 70 mm, as measured from a point of intersection 27, 27' between a part 18A, 18A' of the material of the standing gather being attached to the topsheet 11 and a part 18B, 18B' of the material of the standing gather being non-attached to the topsheet 11 and to the closest longitudinal side edge 3, 3' of the insert.

The elastic thread 16, 16' of the first 15 and second 15' standing gather respectively is raised above the user facing surface of the topsheet 11, such as at least 20 mm and less than 70 mm above the user facing surface of the topsheet 11.

Figure 3:
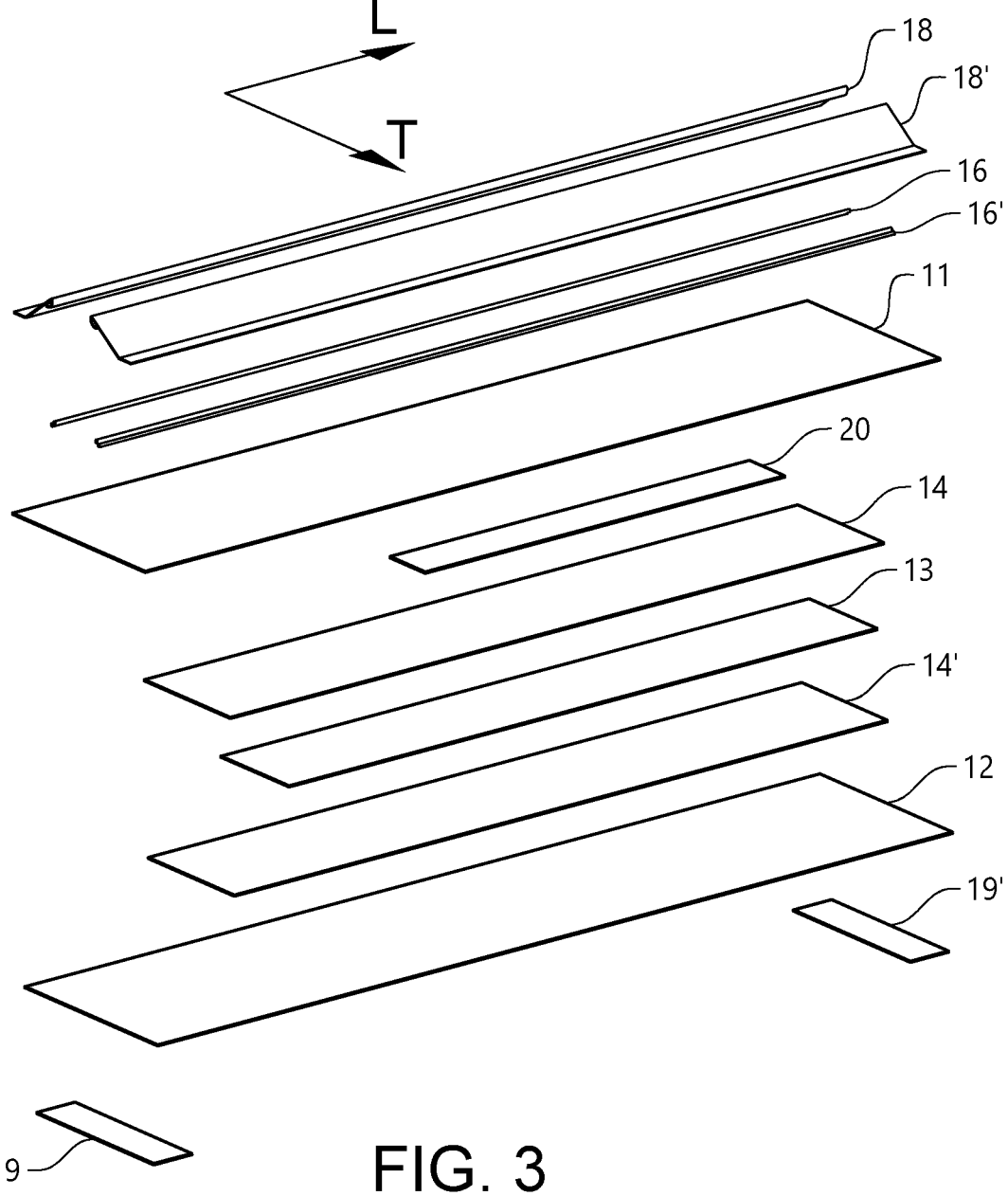
FIG. 3 shows an exploded view of the layers of the insert according to the present disclosure.

FIG. 3 discloses an exploded view of the materials of the disposable insert 1. FIG. 3 shows from above the materials 18, 18' of the standing gathers 15, 15' and the elastic threads 16, 16'. FIG. 3 further shows the topsheet 11, the acquisition layer 20, the upper core cover layer 14, the absorbent component 13, the lower core cover layer 14', the backsheet 12 and the strips of loop material 19, 19'.

Various types of materials may be used for the absorbent insert.

The strips of loop material on the backsheet may have any type of loop surface structure, which is here to be understood to encompass a surface structure to which a hook material of a hook and loop fastening system is attachable. Accordingly, a loop surface structure may include fibers or threads extending from a surface and back into the surface to define genuine loops, as well as a surface structure including fibers or threads extending out from a surface and having loose ends, which fibers or threads entangle with each other. Upon attachment of the respective hook members the hook surface structure engages with the loop surface structure providing a releasable attachment between the elements. The loop material may also be a nonwoven material or a nonwoven material with a backing of an elastic film. The basis weight of the loop material may be 15-70 gsm, such as 30-60 gsm.

The topsheet is arranged to face the wearer of the absorbent insert when worn. The topsheet may be formed by a fluid permeable nonwoven fabric or film which is made of thermoplastic synthetic fibers. The topsheet may be sufficiently liquid-permeable to allow discharged body fluids to penetrate through the thickness of the topsheet. Also, the topsheet may be suitably manufactured from a material which is compliant and soft feeling to the skin of the wearer. The topsheet may consist of a single layer or have a laminate structure comprising a plurality of layers, for example, two or more layers. The layers may be made of the same material, or some or all the layers may be made of different materials.

The layer of the topsheet or, for the case of a laminate structure, one, some or all layers of the topsheet may be a nonwoven material, a perforated plastic film, a plastic or textile mesh, or a liquid permeable foam layer.

The layer of the topsheet or, for the case of a laminate structure, one, some, or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers.

The topsheet may have a basis weight in the range of 8-40 g/m². However, the disclosure is not limited to topsheets having this basis weight only.

The material of the standing gathers may be a liquid impermeable nonwoven material. The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range 10-25 gsm. The elastic thread for the standing gather may be a PP or PP/PE elastic thread, such as sold under the Trademark LYCRA and SPANDEX of 500-850 dtex.

The backsheet may be constituted by a liquid-impermeable and breathable layer such as a polymeric film, for example a film of polyethylene or polypropylene. According to different embodiments, the materials which may be used for the backsheet include thin and flexible fluid impermeable plastic films, or fluid impermeable nonwoven materials, fluid impermeable foams and fluid impermeable laminates.

The backsheet may be formed by a single layer, but may alternatively be formed by a multi-layered structure, i.e. a laminate, wherein at least one layer is fluid impermeable. Furthermore, the backsheet may be elastic in any direction.

Furthermore, the backsheet may have a laminate structure comprising a liquid barrier sheet and a nonwoven layer arranged on top of each other (not shown in detail in the drawings), wherein the nonwoven layer is arranged at an outer side away from the wearer of the absorbent insert when worn. The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range of 5-40 $g/m^2$.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers. The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo and/or mechanical bonding, such as thermo-sealing, ultrasonic bonding, such as ultrasonic welding, an adhesive or adhesives, stitching or the like. The liquid barrier sheet may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes. The liquid barrier sheet may have a basis weight of 8-30 gsm.

Regarding the choice of materials for the various layers in the absorbent insert, the materials may be chosen for the bonding process to form seams. For example, if ultrasonic welding is chosen for joining the upper and lower core cover sides, the chosen materials for the core cover may be adapted to form a secure bond during ultrasonic welding.

The absorbent core is provided between the topsheet and the backsheet to absorb the liquid, such as urine or other bodily fluids, which has passed through the topsheet. The absorbent core may be made of one layer only, made from any suitable absorbent or liquid uptake material, such as one or more layers of cellulose fluff pulp, foam, fiber waddings or the like.

The absorbent core comprises an absorbent component enclosed by a core cover. The absorbent component is sandwiched between the upper and lower core cover side. The disclosure is not limited to a core wrap comprising two core cover layers. The core cover may be of one single material layer. The absorbent component may be enclosed by one core cover layer folded in two, or enclosed by a continuous core cover sheet, thereby providing upper and lower core cover sides for wrapping the absorbent component.

The upper core cover side and the lower core cover side may be attached to each other by various technologies, for example, by thermo and/or mechanical bonding, such as thermo-sealing, ultrasonic bonding and in combination with an adhesive or adhesives, stitching or the like.

The absorbent component may comprise suitable amounts of superabsorbent particles. Such superabsorbent material is well known in the field of absorbent articles, constituted by a water-swellable and water-insoluble material which is capable of absorbing large quantities of fluid upon formation of a hydrogel. The absorbent component may contain superabsorbent material in the form of fibers or particles of absorbent polymer material. For example, the superabsorbent material may be surface cross-linked, partially neutralized polyacrylates. The superabsorbent material, e.g., the superabsorbent fibers or particles, may be mixed with other absorbent or liquid uptake material or materials, such as cellulose fluff pulp, and/or arranged in pockets or layers in the absorbent core. The amount of superabsorbent material and pulp in the absorbent core may be 0-50% by weight pulp fibers and 50-100% by weight superabsorbent material.

The core cover as mentioned above may be made of nonwoven material, with a basis weight of 5-20 $g/m^2$. The nonwoven material may be of thermoplastic polymer fibers or filaments. The nonwoven may be formed by a variety of different processes such as spunbonding, airlaying, meltblowing or bonded carded web formation processes. The core cover may be of an SMS (spunbond/meltblown/spunbond) or SS (spunbond/spunbond) nonwoven material and may be of polypropylene or bicomponent fibers of polypropylene and polyethylene, or of a combination of the same.

The absorbent core may further comprise components for improving the properties of the absorbent core. For example, the absorbent core may comprise a binder or binders, such as binder fibers.

Furthermore, as known by the skilled person, the various layers of the absorbent insert may be attached by means of adhesive material. Such adhesive is not shown in the drawings.

One or more additional layers may be provided in the absorbent insert. For example, an acquisition layer may be arranged between the absorbent core and the topsheet. Such an additional layer may for example be in the form of an airlaid layer, a spunlace layer, a high-loft, foam or any other type of material layer which may be used in an absorbent insert to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by means of pressure and vacuum. The acquisition layer may have a basis weight of 15-100 gsm.

Figure 4:
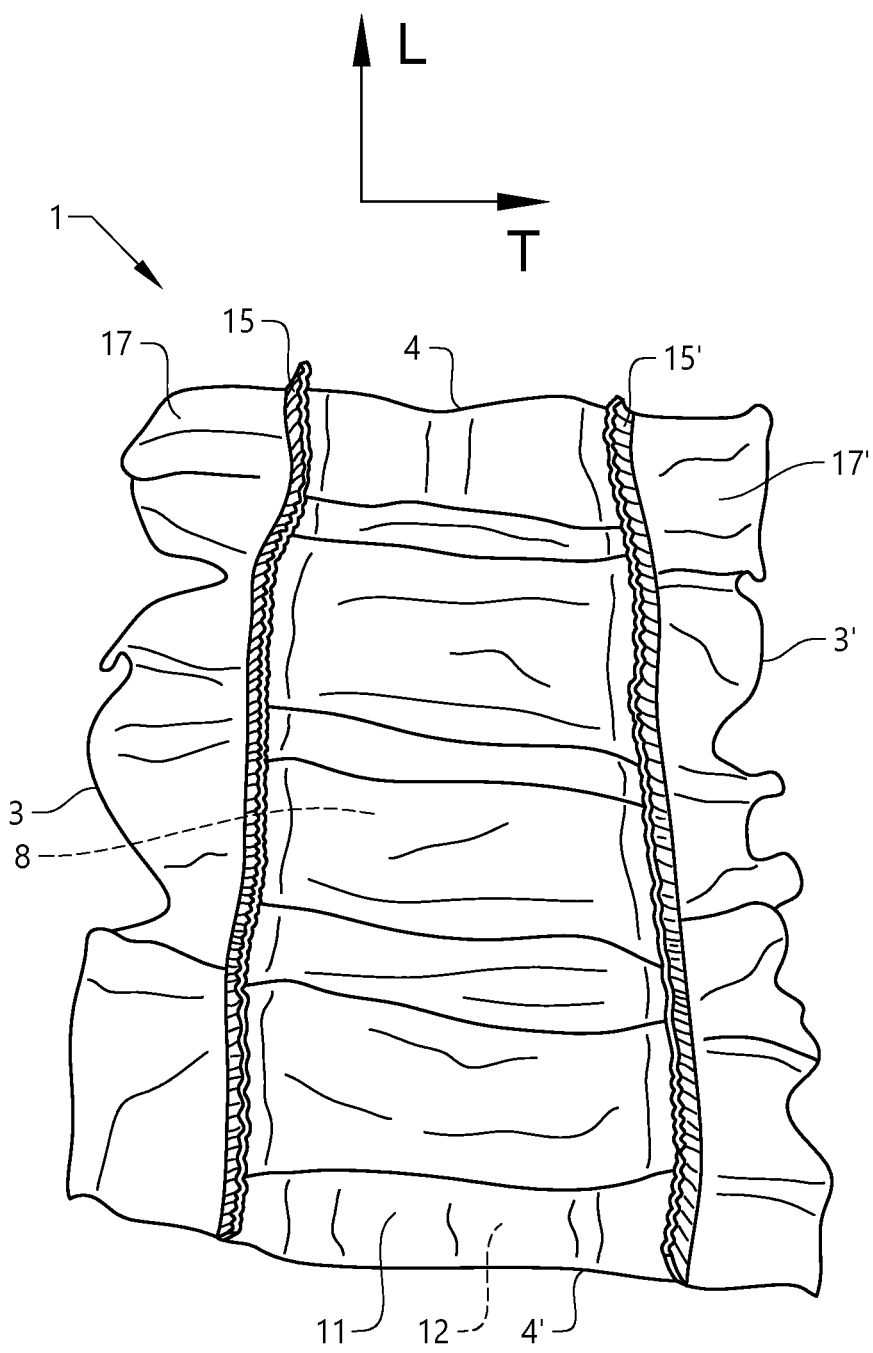
FIG. 4 shows an absorbent insert according to the present disclosure.

FIG. 4 discloses a view from the topsheet 11 side of the absorbent insert 1 having longitudinal 3, 3' and transversal 4, 4' side edges. The first 15 and second 15' standing gathers extend along the longitudinal side edges 3, 3' of the insert 1. The first 17 and second 17' side leakage flaps extends transversally outside the first 15 and second 15' standing gathers respectively. The first 17 and second 17' side leakage flaps respectively lacks elastics at the free outer longitudinal 3, 3' side edge.

Figure 5:
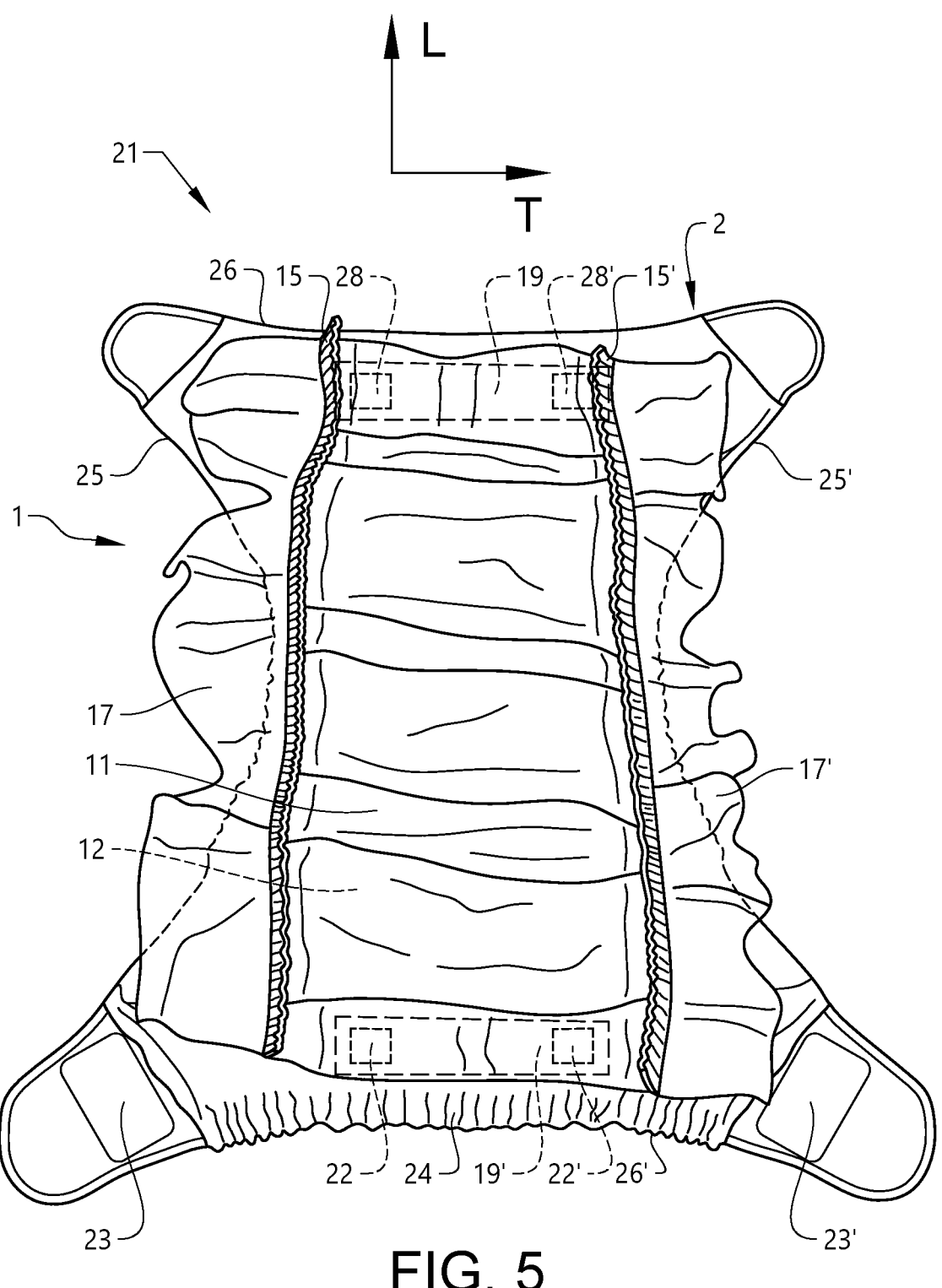
FIG. 5 shows a wearable absorbent article comprising a reusable shell and a disposable insert.

FIG. 5 discloses the absorbent insert 1 of FIG. 4 in a reusable shell 2. The reusable shell 2 has longitudinal 25, 25' and transversal 26, 26' side edges and an inner surface and an outer surface. FIG. 5 is an illustration of the reusable shell 2 as seen from the inner surface facing the user when worn.

The reusable outer shell 2 is an outer shell that is capable of being reused multiple times. The reusable outer shell may be a washable outer shell, capable of being washed multiple times without essential shrinkage or other damage. The outer shell may be made from a washable material such as a washable fabric. The outer shell may be made of one or more of the following materials: polyester, viscose, polyamide and/or cotton. The outer shell may be a stretchable outer shell, i.e. being made of a stretchable material. The outer shell may be an elastic shell, being elastic in the longitudinal direction L and/or the transverse direction T of the outer shell.

The outer shell 2 comprises a front region, a crotch region and a rear region. A front hook member 28, 28' is arranged in the front portion of the inner surface of the outer shell 2 and a rear hook member 22, 22' arranged in the back portion of the inner surface of the outer shell 2. The rear hook member 22, 22' comprises a first rear hook member part 22 and a second 22' rear hook member part. The front hook member 28, 28' comprises a first front hook member part 28 and a second front hook member part 28'. The first front hook member part 28 and the second front hook member part 28' are spaced apart from each other and are arranged on a respective side of a longitudinal centerline of the outer shell. The first rear hook member part 22 and the second rear hook member part 22' may be spaced apart from each other and are arranged on a respective side of a longitudinal centerline of the outer shell. The front hook member 28, 28' has a length and the rear hook 22, 22' member has a length, the respective lengths each extending in the longitudinal direction L. The length of the rear hook member 22, 22' may be greater than the length of the front hook member 28, 28'.

The front 28, 28' and rear 22, 22' hook members may comprise any hook-type material with a hook surface structure and the terms hook members are to be interpreted as encompassing the hook part of a hook and loop fastening system, e.g., known as a VELCRO® system. The "hooks" may have many different shapes which are adapted to engage with a loop part of the hook and loop fastening system. The hooks may, purely as an example, have a J-shape, mushroom shape, and palm tree shape.

The outer shell 2 comprises a first hook member 23 in the rear region provided in a first rear transverse corner region of the shell 2 and a second hook member 23' provided in a second rear transverse corner region of the shell 2. The outer shell 2 comprises a hook attachment zone on the outer surface in the front region of the outer shell (not shown). The hook attachment zone may comprise a loop material. The first 23 and second 23' hook members are adapted to be attached to the hook attachment zone to form a waist opening when the shell 2 is worn.

The first 23 and second 23' hook members may comprise any hook-type material with a hook surface structure and the hook attachment zone may comprise any loop surface structure, and the terms hook members are to be interpreted as encompassing the hook part of a hook and loop fastening system, e.g., known as a VELCRO® system. The "hooks" may have many different shapes which are adapted to engage with a loop part of the hook and loop fastening system. The hooks may, purely as an example, have a J-shape, mushroom shape, and palm tree shape. The hook attachment zone may comprise any type of loop surface structure, which is here to be understood to encompass a surface structure to which a hook material of a hook and loop fastening system is attachable. Accordingly, a loop surface structure may include fibers or threads extending from a surface and back into the surface to define genuine loops, as well as a surface structure including fibers or threads extending out from a surface and having loose ends, which fibers or threads entangle with each other. Upon attachment of the respective hook members the hook surface structure engages with the loop surface structure providing a releasable attachment between the elements.

The outer shell may comprise leg elastics arranged along a respective longitudinal side edge of the outer shell in the crotch region (not shown) and waist elastics 24 arranged along a rear transverse edge 26' in the rear region of the outer shell 2.

To releasably attach the absorbent insert 1 to the outer shell 2, the outer shell 2 comprises a front hook member 28, 28' and a rear hook member 22, 22' arranged on the inside surface of the outer shell 2 and to be attached to the front and rear loop members or strips of loop material 19, 19' attached to the garment facing side of the backsheet 12 of the insert 1.

The disclosure may be varied within the scope of the appended claims. For example, the materials and dimensions used for the different layers forming the absorbent insert may be varied, as indicated above.

The invention claimed is:

1. A disposable absorbent insert for a reusable outer shell, the insert having an extension in the longitudinal direction and the transversal direction, longitudinal and transversal side edges and having a front portion, a back portion and a crotch portion located between the front and the back portions, the insert comprising:

an absorbent core having longitudinal and transversal side edges and being sandwiched between a liquid-permeable and user facing topsheet and a liquid-impermeable and garment facing backsheet, and wherein the absorbent core comprises:

an absorbent component enclosed by a core cover comprising an upper and a lower side, the insert comprising a first longitudinal extending standing gather along a first longitudinal side edge of the insert and a second longitudinal extending standing gather along a second longitudinal side edge of the insert, wherein the topsheet extends transversely outside the first longitudinal extending standing gather to form a first side leakage flap and the topsheet extends transversely outside the second longitudinal extending standing gather to form a second side leakage flap, and the first and second side leakage flaps lack elastics.

2. An absorbent insert according to claim 1, wherein the first side leakage flap extends along the whole longitudinal length of the first longitudinal side edge of the insert and the second side leakage flap extends along the whole longitudinal length of the second longitudinal side edge of the insert.

3. An absorbent insert according to claim 1, wherein the first and second side leakage flaps are extensions of the topsheet and the backsheet.

4. An absorbent insert according to claims 3, wherein the topsheet and the backsheet in the first and second side leakage flaps are attached to each other.

5. An absorbent insert according to claim 1, wherein the first longitudinal extending standing gather along the first longitudinal side edge of the insert comprises a first sheet of material and an elastic thread and the second longitudinal extending standing gather along the second longitudinal side edge of the insert comprises a second sheet of material and an elastic thread.

6. An absorbent insert according to claim 5, wherein the first and second side leakage flaps are extensions of the backsheet and the material of the first and second respectively standing gather.

7. An absorbent insert according to claim 6, wherein the material of the first and second respectively standing gather are attached to the backsheet in the first and second side leakage flaps.

8. An absorbent insert according to claim 5, wherein the first and second side leakage flaps are extensions of topsheet, backsheet and the material of the first and second respectively standing gather.

9. An absorbent insert according to claim 5, wherein the material of the first and second standing gather respectively comprises two layers of material.

10. An absorbent insert according to claim 5, wherein the material of the first and second standing gather is attached to the material of the topsheet in the first and second side leakage flap respectively.

11. An absorbent insert according to claim 5, wherein the material of the first standing gather comprises a part being attached to the topsheet and a part being non-attached to the topsheet comprising the elastic thread and the material of the second standing gather comprises a part being attached to the topsheet and a part being non-attached to the topsheet comprising the elastic thread.

12. An absorbent insert according to claim 11, wherein the transverse extension of the first and second side leakage flaps respectively is at least 10 mm and less than 70 mm as measured from a point of intersection between the part of the material of the standing gather being attached to the topsheet and the part of the material of the standing gather being non-attached to the topsheet.

13. An absorbent insert according to claim 11, wherein the transverse extension of the first and second side leakage flaps respectively is at least 15 mm and less than 60 mm as measured from a point of intersection between the part of the material of the standing gather being attached to the topsheet and the part of the material of the standing gather being non-attached to the topsheet.

14. An absorbent insert according to claim 11, wherein the transverse extension of the first and second side leakage flaps respectively is at least 25 mm and less than 50 mm as measured from a point of intersection between the part of the material of the standing gather being attached to the topsheet and the part of the material of the standing gather being non-attached to the topsheet.

15. An absorbent insert according to claim 1, wherein the insert lacks exterior leg gathers.

16. An absorbent insert according to claim 5, wherein the elastic thread of the first and second standing gather respectively is raised above the user facing surface of the topsheet.

17. An absorbent insert according to claim 5, wherein the elastic thread of the first and second standing gather respectively is raised at least 20 mm and less than 70 mm above the user facing surface of the topsheet.

18. An absorbent insert according to claim 1, wherein the first and second side leakage flap respectively lacks elastics at a free outer first and second longitudinal side edge of the insert.

19. An absorbent insert according to claim 1, wherein the topsheet and the backsheet each extends longitudinally outside the transversal side edges of the core in the front and back portions respectively of the insert.

20. An absorbent insert according to claim 19, wherein a longitudinal extension of the topsheet and backsheet is greater in the back portion of the insert than in the front portion of the insert.

21. An absorbent insert according to claim 19, wherein a longitudinal extension of the topsheet and backsheet in the back portion is 2 to 6 times greater than in the front portion of the insert.

22. An absorbent insert according to claim 1, wherein a strip of loop material is attached to the backsheet near the transversal side edge of the front and back portions respectively of the insert.

23. An absorbent insert according to claim 22, wherein the strip of loop material extends over 50-100% of the transverse side of the insert.

24. An absorbent insert according to claim 22, wherein the longitudinal extension of the strip of loop material is 10 to 50 mm.

25. An absorbent insert according to claim 22, wherein the longitudinal extension of the strip of loop material is greater in the back portion than in the front portion of the insert.

26. An absorbent insert according to claim 22, wherein the strip of loop material has the same free transversal side edge as materials of the topsheet and the backsheet.

27. An absorbent insert according to claim 1, wherein the core has a rectangular shape.

28. An absorbent insert according to claim 1, wherein the insert has a rectangular shape.

29. A wearable absorbent article comprising a reusable shell, to be worn by a wearer, and a disposable insert according to claim 1.

* * * * *